(12) United States Patent
Kuroda et al.

(10) Patent No.: US 10,905,480 B2
(45) Date of Patent: Feb. 2, 2021

(54) BONE PLATE AND BONE PLATE SYSTEM

(71) Applicant: OLYMPUS TERUMO BIOMATERIALS CORP., Tokyo (JP)

(72) Inventors: Koichi Kuroda, Kanagawa (JP); Mitsuya Urata, Kanagawa (JP); Ryohei Takeuchi, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 69 days.

(21) Appl. No.: 16/200,760

(22) Filed: Nov. 27, 2018

(65) Prior Publication Data

US 2019/0090921 A1    Mar. 28, 2019

Related U.S. Application Data

(63) Continuation of application No. PCT/JP2016/065960, filed on May 31, 2016.

(51) Int. Cl.
*A61B 17/80* (2006.01)
*A61B 17/86* (2006.01)
*A61B 17/88* (2006.01)

(52) U.S. Cl.
CPC .......... *A61B 17/8061* (2013.01); *A61B 17/80* (2013.01); *A61B 17/8057* (2013.01); *A61B 17/8095* (2013.01); *A61B 17/864* (2013.01); *A61B 17/8897* (2013.01)

(58) Field of Classification Search
CPC ............................ A61B 17/8061; A61B 17/80
See application file for complete search history.

(56) References Cited

U.S. PATENT DOCUMENTS 5,938,664 A    8/1999    Winquist et al.
5,954,722 A    9/1999    Bono
(Continued)

FOREIGN PATENT DOCUMENTS

CA    2 266 830 A1    9/1999
CN    1832706 A    9/2006
(Continued)

OTHER PUBLICATIONS

International Search Report dated Aug. 9, 2016 issued in PCT/JP2016/065960.
(Continued)

*Primary Examiner* — Christian A Sevilla
(74) *Attorney, Agent, or Firm* — Scully, Scott, Murphy & Presser, P.C.

(57) ABSTRACT

The bone plate of the present invention includes a body portion to be fixed to an obliquely anterior medial surface of the tibia below the osteotomy surface; a wide portion to be fixed to an outer peripheral surface of the tibia at a higher position than the osteotomy surface; a connecting portion that connects the body portion and the wide portion; and a plurality of screw holes arrayed in the body portion, the wide portion and the connecting portion. An inner surface that extends from the wide portion to the connecting portion and faces the tibia has a continuous curved shape twisted about an axis along the longitudinal direction of the tibia. The wide portion is offset in an outward plate thickness direction with respect to the body portion.

9 Claims, 8 Drawing Sheets

(56) References Cited

U.S. PATENT DOCUMENTS

| | | | |
|---|---|---|---|
| 6,623,486 B1* | 9/2003 | Weaver | A61B 17/8057 606/281 |
| 8,864,802 B2* | 10/2014 | Schwager | A61B 17/8061 606/286 |
| D852,957 S | 7/2019 | Horan et al. | |
| 2002/0013587 A1 | 1/2002 | Winquist et al. | |
| 2002/0065516 A1 | 5/2002 | Winquist et al. | |
| 2002/0156474 A1 | 10/2002 | Wack et al. | |
| 2004/0030339 A1 | 2/2004 | Wack et al. | |
| 2004/0059334 A1 | 3/2004 | Weaver et al. | |
| 2004/0059335 A1 | 3/2004 | Weaver et al. | |
| 2004/0186477 A1 | 9/2004 | Winquist et al. | |
| 2005/0010226 A1 | 1/2005 | Grady, Jr. et al. | |
| 2005/0049594 A1 | 3/2005 | Wack et al. | |
| 2005/0080421 A1 | 4/2005 | Weaver et al. | |
| 2005/0261688 A1 | 11/2005 | Grady, Jr. et al. | |
| 2007/0162015 A1* | 7/2007 | Winquist | A61B 17/8085 606/283 |
| 2007/0233106 A1 | 10/2007 | Horan et al. | |
| 2008/0132960 A1 | 6/2008 | Weaver et al. | |
| 2008/0300637 A1* | 12/2008 | Austin | A61B 17/8061 606/290 |
| 2010/0030277 A1* | 2/2010 | Haidukewych | A61B 17/8061 606/286 |
| 2010/0274247 A1 | 10/2010 | Grady, Jr. et al. | |
| 2011/0202093 A1 | 8/2011 | Grady, Jr. et al. | |
| 2011/0313422 A1 | 12/2011 | Schwager et al. | |
| 2012/0265254 A1 | 10/2012 | Horan et al. | |
| 2013/0172943 A1 | 7/2013 | Austin et al. | |
| 2013/0296943 A1 | 11/2013 | Grady, Jr. et al. | |
| 2014/0121710 A1 | 5/2014 | Weaver et al. | |
| 2015/0066095 A1 | 3/2015 | Austin et al. | |
| 2016/0074081 A1 | 3/2016 | Weaver et al. | |
| 2016/0175018 A1 | 6/2016 | Grady, Jr. et al. | |
| 2017/0007304 A1 | 1/2017 | Kuroda et al. | |
| 2018/0000528 A1 | 1/2018 | Austin et al. | |
| 2018/0199966 A1 | 7/2018 | Grady, Jr. et al. | |
| 2018/0250044 A1 | 9/2018 | Austin et al. | |
| 2018/0250045 A1 | 9/2018 | Austin et al. | |
| 2018/0250046 A1 | 9/2018 | Austin et al. | |
| 2018/0317984 A1 | 11/2018 | Horan et al. | |
| 2020/0237420 A1 | 7/2020 | Grady, Jr. et al. | |
| 2020/0360064 A1 | 11/2020 | Horan et al. | |

FOREIGN PATENT DOCUMENTS

| | | | |
|---|---|---|---|
| EP | 0 947 176 | A2 | 10/1999 |
| EP | 1250892 | A2 | 10/2002 |
| EP | 2389884 | A1 | 11/2011 |
| EP | 3123971 | A1 | 2/2017 |
| JP | 2003509107 | A | 3/2003 |
| JP | 4149130 | B2 | 9/2008 |
| JP | 4368560 | B2 | 11/2009 |
| JP | 2011245306 | A | 12/2011 |
| JP | 1572388 | S | 3/2017 |
| TW | I411424 | B | 10/2013 |
| WO | 9905968 | A1 | 2/1999 |
| WO | 2001019267 | A1 | 3/2001 |
| WO | 2004/107957 | A2 | 12/2004 |
| WO | 2007/100513 | A2 | 9/2007 |
| WO | 2010/014701 | A1 | 2/2010 |
| WO | 2015146866 | A1 | 10/2015 |

OTHER PUBLICATIONS

Takeuchi, R. et al., "Medial Open Wedge and Lateral Closed Wedge High Tibial Osteotomy that Enable Full-Weight-Bearing Walking from Early Postoperative Period", MC Orthopaedics, 2013, vol. 26, No. 4, pp. 1-9, with English-language translation.

Takeuchi, R. et al., "A Novel Closed-Wedge High Tibial Osteotomy Procedure to Treat Osteoarthritis of the Knee: Hybrid Technique and Rehabilitation Measures", Arthroscopy Techniques, Aug. 2014, vol. 3, No. 4, pp. e431-e437.

Asia Bone Curve Health Unit Company Ltd., "Proximal Lateral Tibial Locking Plate", Retrieved from the Internet, URL: http://www.abchuc.com/en/san-pham/nep-khoa-mam-chay-256.html, 2 pages.

DePuy Synthes, "TomoFix Lateral High Tibia Plate", Retrieved from the Internet, URL: https://www.depuysynthes.com/hcp/trauma/products/qs/tomofix-lateral-high-tibia-plate, 2 pages.

DePuy Synthes Trauma, "Tomofix Osteotomy Technique Guide", Retrieved from the Internet, URL: https://www.orthopedierijnmond.nl/uploads/TOMOFIX%20OSTEOTOMIE.pdf, 38 pages.

DePuy Synthes Trauma, "3.5 MM VA-LCP Proximal Tibia Plate System", Retrieved from the Internet, URL:http://synthes.vo.llnwd.net/o16/LLNWMB8/US%20Mobile/Synthes%20North%20America/Product%20Support%20Materials/Technique%20Guides/SUTG3.5VALCPProxTibJ11571D.pdf, 63 pages.

Extended Supplementary European Search Report dated Dec. 3, 2019 in European Patent Application No. 16 90 3946.8.

Chinese Office Action dated Sep. 27, 2020 in Chinese Patent Application No. 201680086048.6.

Indian Office Action dated Dec. 2, 2020 in Indian Patent Application No. 201817043565.

* cited by examiner

BONE PLATE AND BONE PLATE SYSTEM

CROSS-REFERENCE TO RELATED APPLICATIONS

This is a continuation of International Application PCT/JP2016/065960, with an international filing date of May 31, 2016, which is hereby incorporated by reference herein in its entirety.

TECHNICAL FIELD

The present invention relates to a bone plate and a bone plate system.

BACKGROUND ART

Heretofore, in order to fix bone fractures and osteotomy sites and to accelerate healing and joining of bones, a bone plate system that includes a bone plate and screws for fixing the bone plate to the bone has been used (for example, see PTL 1).

Such a bone plate system is, for example, used in high tibial osteotomy (HTO) to treat knee osteoarthritis. High tibial osteotomy is a surgical procedure that involves cutting a patient's own bone to induce a slight angular change so as to change the direction of the load, which is biased toward the medial side due to a varus deformity, to the lateral side and correct the alignment.

There are several types of high tibial osteotomy: an open wedge HTO technique that involves incising a bone from the medial side to the lateral side of the tibia, expanding the incision, and inserting a trapezoidal or wedge-shaped artificial bone or the like thereinto so as to carry out angular correction, and a closed wedge HTO technique that involves cutting out a wedge-shaped block from the bone, from the lateral side of the tibia, so as to shorten the bone and carry out angular correction.

In recent years, a procedure called hybrid HTO that has the advantages of both the open wedge technique and the closed wedge technique has been performed to treat advanced medial osteoarthritis cases involving large correction angles or accompanied by osteoarthritis in the patella or femoral joint.

International Publication No. 2015/146866 discloses a bone plate system used in the open wedge technique.

Furthermore, Japanese Patent Publication No. 4368560 discloses a bone plate system used to mend and fix fractured segments in the case of fracture of a long bone, such as the femur or tibia. In the bone plate system described in Japanese Patent Publication No. 4368560, when the bone plate is fixed to an epiphyseal region with screws, the axis directions of the screws can be changed by turning the screws.

SUMMARY OF INVENTION

An object of the present invention is to provide a bone plate and a bone plate system that have an optimized structure in view of conformance to the corrected tibial shape after hybrid HTO.

According to one aspect of the present invention, there is provided a bone plate comprising: a strip-shaped body portion to be fixed to a portion of the lateral surface of the tibia below an osteotomy surface formed in the lateral surface of the tibia, the body portion extending along a longitudinal direction of the tibia; a wide portion wider than the body portion and to be fixed along an outer peripheral surface of the head of the tibia at a higher position than the osteotomy surface; a connecting portion that connects the body portion and the wide portion; and a plurality of screw holes arrayed in the wide portion, the body portion, and the connecting portion with spaces between one another and penetrate therethrough in a plate thickness direction, wherein an inner surface that extends from the wide portion to the connecting portion and faces the tibia has a curved shape that substantially fits a three-dimensional contour of the tibia in a continuous manner while being twisted about an axis along the longitudinal direction of the tibia, the wide portion is offset in an outward plate thickness direction with respect to the body portion, and when the bone plate is attached to the tibia, a curvature of a side surface of the connecting portion that follows the posterior surface of the tibia is larger than a curvature of a side surface of the connecting portion that follows the anterior surface of the tibia.

In the aspect described above, the plurality of screw holes may include a plurality of first screw holes formed in the wide portion with spaces between one another, and a plurality of second screw holes formed in the connecting portion with spaces between one another, and a first axis, which is an axis of one of the plurality of the first screw holes that is located at a tibial posterior surface-side position when the bone plate is attached to the tibia, and a second axis, which is an axis of one of the plurality of the second screw holes that is located at a tibial anterior surface-side position when the bone plate is attached to the tibia, may lie along substantially the same plane.

In the aspect described above, an angle formed between a straight line connecting an upper end portion and lower end portion of the bone plate in the longitudinal direction and a first plane that includes a straight line that defines an arraying direction of the plurality of first screw holes and an axis direction of the first screw holes may be 80° or more and 90° or less.

In the aspect described above, an offset amount of the offset may be 15 mm or more and 25 mm or less.

In the aspect described above, a total length in the longitudinal direction may be 100 mm or more and 120 mm or less and preferably 95 mm or more and 105 mm or less.

According to another aspect of the present invention, there is provided a bone plate system comprising: any of the bone plates described above and a plurality of screws to be respectively fastened to the plurality of screw holes in the bone plate so as to fix the bone plate to the tibia.

In the aspect described above, the bone plate may have a plate thickness of 3±1 mm, and the bone plate system may be configured such that, in a state in which the bone plate is fastened with the plurality of screws, an amount of deflection of the bone plate when a vertical load is applied in a longitudinal axis direction of the bone plate is 0.5 mm±0.3 mm/kgf.

In the aspect described above, the bone plate and the screws may contain a highly biocompatible material.

In the aspect described above, the screws may be hollow screws each having a through hole through which a guide pin can pass, a thread diameter of the screws may be $\phi 5.0$ mm or more and 5.8 mm or less, a root diameter may be $\phi 4.5$ mm or more and 5.3 mm or less, and a hollow shaft diameter of the hollow screws may be $\phi 1.8$ mm or more and 2.8 mm or less.

DESCRIPTION OF EMBODIMENTS

A bone plate 1 and a bone plate system 2 according to one embodiment of the present invention will now be described with reference to the drawings.

Figure 1:
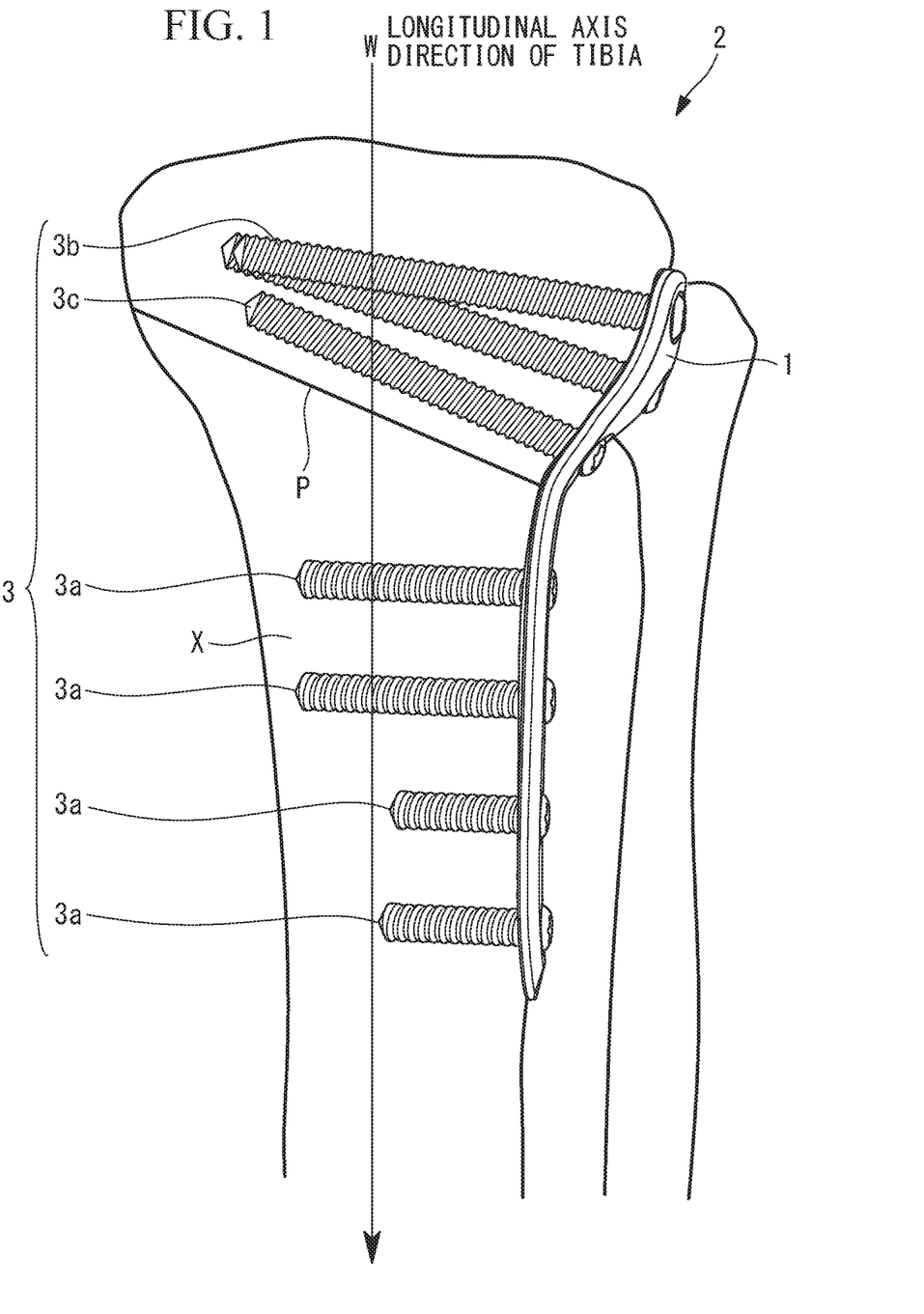
FIG. 1 is a diagram illustrating the overall structure of a bone plate system according to one embodiment of the present invention.

As illustrated in FIG. 1, the bone plate system 2 of this embodiment includes the bone plate 1 and a plurality of screws 3 for fixing the bone plate 1 to a high position of the lateral surface of the tibia X.

The bone plate 1 of this embodiment is used in a so-called hybrid HTO that has advantages of both the open wedge technique and the closed wedge technique performed to treat advanced medial osteoarthritis involving large correction angles or accompanied by osteoarthritis in the patella or femoral joint, and is an elongated strip-shaped component to be fixed to a high position of the lateral surface of the tibia X after the osteotomy.

Figure 2A:
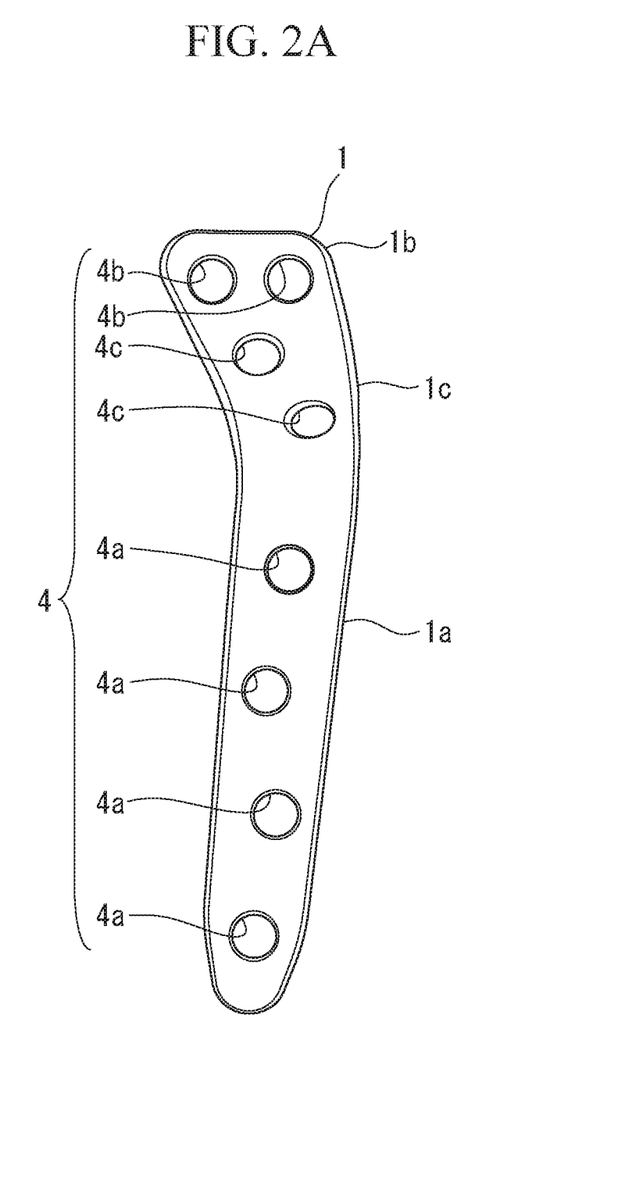
FIG. 2A is a plan view of a bone plate illustrated in FIG. 1.
Figure 2B:
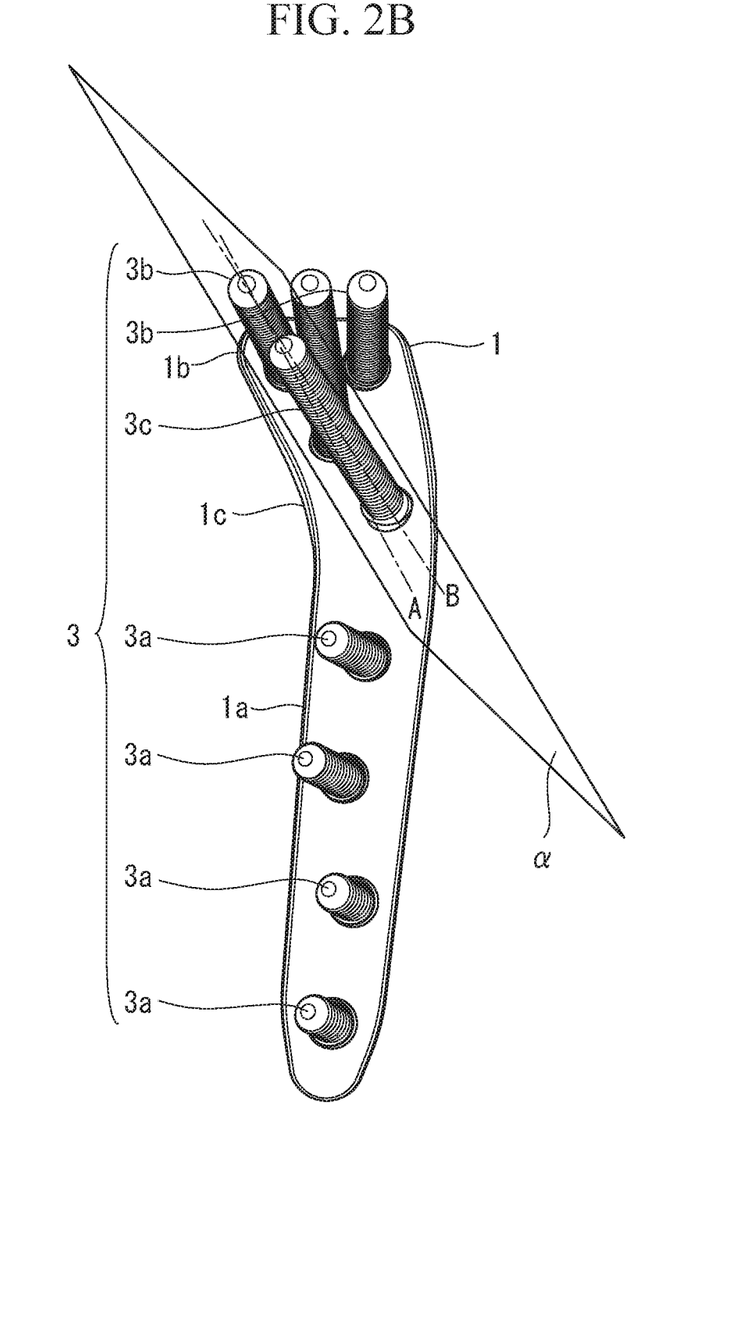
FIG. 2B is a plan view of the bone plate illustrated in FIG. 1 with screws inserted therein.

As illustrated in FIGS. 2A and 2B, the bone plate 1 used in hybrid HTO includes an elongated strip-shaped body portion 1a, a wide portion 1b wider than the body portion 1a, and a connecting portion 1c that connects the body portion 1a and the wide portion 1b. As illustrated in FIG. 2A, the bone plate 1 has a plurality of screw holes 4 which are formed in the wide portion 1b, the body portion 1a, and the connecting portion 1c with spaces between one another and which penetrate the bone plate 1 in the plate thickness direction. The screw holes 4 include a plurality of screw holes 4a formed in the body portion 1a, a plurality of first screw holes 4b formed in the wide portion 1b, and a plurality of second screw holes 4c formed in the connecting portion 1c. FIG. 2A illustrates an example in which four screw holes 4a are formed in the body portion 1a, two screw holes 4b are formed in the wide portion 1b, and two screw holes 4c are formed in the connecting portion 1c; however, the numbers of screw holes are not limited to these and may be decreased or increased.

Figure 4:
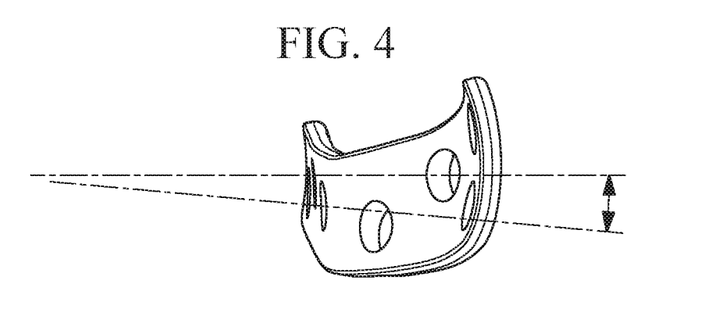
FIG. 4 is a front view of the bone plate illustrated in FIG. 2A.

The body portion 1a is formed to have a strip shape so as to follow a lower position of the lateral surface of the tibia X. In addition, as illustrated in FIG. 4, the inner surface that faces the tibia X from the wide portion 1b to the connecting portion 1c has a continuous curved shape twisted about the axis along the longitudinal direction of the tibia X. In this embodiment, the twist angle of the bone plate is, for example, 13±5° so that the bone plate substantially fits the three-dimensional contour of the tibia X when attached to the tibia X, and when the portion where the twist is the largest is near the screw hole 4c, the screw fixing strength and the plate shape conformability can both be achieved.

Figure 3A:
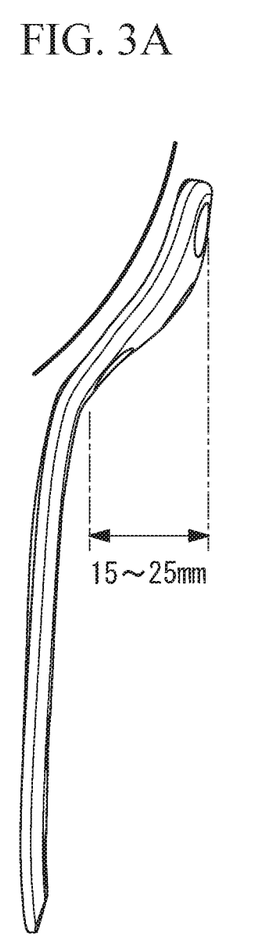
FIG. 3A is a side view of the bone plate illustrated in FIG. 1.

Furthermore, as illustrated in FIG. 3A, the wide portion 1b is outwardly offset in the plate thickness direction with respect to the body portion 1a. The offset amount is 15 mm or more and 25 mm or less in this embodiment.

Figure 3B:
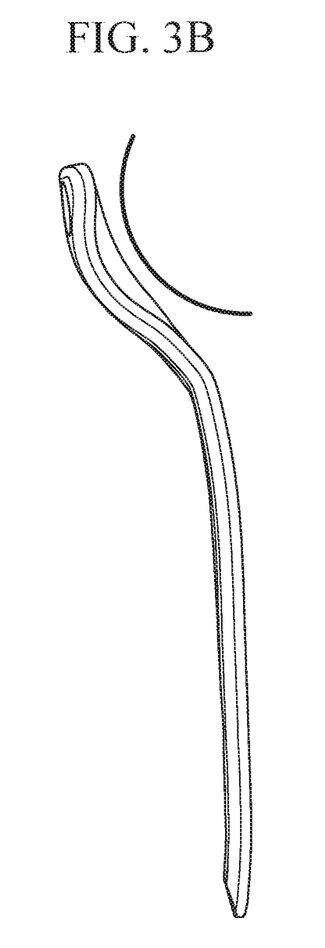
FIG. 3B is a side view of the bone plate illustrated in FIG. 1.

As illustrated in FIGS. 3A and 3B, the bone plate 1 of this embodiment is formed so that the side surface curvature of the connecting portion 1c as viewed from one side surface differs from that viewed from the other side surface. Specifically, the bone plate 1 is formed so that the curvature of the side surface of the connecting portion 1c on the side that follows the posterior surface of the tibia X (FIG. 3B) when the bone plate 1 is attached to the tibia X is larger than the curvature of the side surface of the connecting portion 1c on the side that follows the anterior surface of the tibia X (FIG. 3A) when the bone plate 1 is attached to the tibia X. In this embodiment, for example, the radius of curvature of the side that follows the posterior surface of the tibia X is set to 12.5±7.5 mm, and the radius of curvature of the side that follows the anterior surface is set to 90±30 mm.

As illustrated in FIG. 2B, screws 3 are inserted into the screw holes 4 from one side toward the other side in the plate thickness direction.

As illustrated in FIG. 2B, screws 3a are inserted into the screw holes 4a formed in the body portion 1a, and screws 3c are inserted into the screw holes 4c formed in the connecting portion 1c. Screws 3b are inserted into the screw holes 4b in the wide portion 1b.

Furthermore, as illustrated in FIG. 2B, the threading angles of the respective screw holes are set so that axis A of the screw 3b fastened to the screw hole 4b (on the left side in FIG. 2A), which is one of the screw holes 4b in the wide portion 1b on the side where the side surface curvature is large, and axis B of the screw 3c fastened to the screw hole 4c (on the right side in FIG. 2A), which is one of the screw holes 4c formed in the connecting portion 1c on the side where the side surface curvature is large, lie along substantially the same plane α.

The effects of the bone plate 1 and the bone plate system 2 of this embodiment having the above-described structures are described below.

In order to perform high tibial osteotomy for knee osteoarthritis by the hybrid HTO technique using the bone plate system 2 of this embodiment, an incision is formed from a high position of the lateral surface of the tibia X toward the medial side in a direction oblique with respect to the longitudinal axis of the tibia X so as to form a first osteotomy surface, and then another incision is formed from the lateral surface of the tibia X at a position remote from the osteotomy surface in the longitudinal axis direction toward the medial side so as to form a second osteotomy surface, and then a wedge-shaped bony block between the first osteotomy surface and the second osteotomy surface is removed with a particular tool. Then, the first osteotomy surface and the second osteotomy surface are brought together to close the wedge so as to turn the axis direction of the tibia outward, and subsequently, the bone plate 1 is placed along a transition portion of the lateral surface of the tibia X between the shaft portion and the end portion, and is fixed thereat. Specifically, as illustrated in FIG. 1, the body portion 1a of the bone plate 1 is applied to a portion of the lateral surface of the tibia X below a closure surface P, which is formed by bringing together the first osteotomy surface and the second osteotomy surface for closure, in the longitudinal direction and the wide portion 1b and the connecting portion 1c are applied to a portion above the closure surface in the longitudinal direction.

Subsequently, the screws 3 are passed from the lateral side toward the medial side in the plate thickness direction through the screw holes 4 in the bone plate 1 and are fastened to the tibia X. As a result, the tibia X, after correction by osteotomy, can support a vertical load through the bone plate 1 bridging the incision and fixed with the screws 3.

The screws 3b inserted into the screw holes 4b in the wide portion 1b are fastened so as to lie on a plane substantially parallel to the tibial articular surface. Thus, the bone plate can be fixed while preventing the tips of screws 3b from being directed toward the tibial articular surface. Moreover, since the tips of the screws 3b can be directed toward a thick portion of the tibia X with a high bone density, the fixability can be improved while maintaining the integrity of the cancellous bone even under poor fixing conditions and degraded bone quality caused by osteoporosis etc.

The bone plate 1 of this embodiment is formed so that the curvature of the side surface of the connecting portion 1c on the side that follows the posterior surface of the tibia X (FIG. 3B) when the bone plate 1 is attached to the tibia X is larger than the curvature of the side surface of the connecting portion 1c on the side that follows the anterior surface of the tibia X (FIG. 3A) when the bone plate 1 is attached to the tibia X; thus, the bone plate 1 can be placed so as to substantially fit the three-dimensional contour of the tibia X after hybrid HTO.

Furthermore, the threading angles of the respective screw holes are set so that axis A of the screw 3b fastened to the screw hole 4b, which is one of the screw holes 4b formed in the wide portion 1b on the side where the side surface curvature is large, and axis B of the screw 3c fastened to the screw hole 4c, which is one of the screw holes 4c formed in the connecting portion 1c on the side where the side surface curvature is large, lie on substantially the same plane; thus, the screws can be placed closer to one another in a direction orthogonal to the direction in which the screws 3 extend, the number of engaging threads can be increased, and thus a more secure fixation is made possible. In addition, when the bone plate 1 is fastened and fixed to the tibia with the screws 3, the tips of the screws 3 can be accurately delivered to a posterior portion of the tibia X where the bone density of the tibia X is high; thus, the fixability of the bone plate 1 to the tibia X can be enhanced.

As illustrated in FIG. 3A, the bone plate 1 of this embodiment can closely follow the lateral surface of the tibia X after correction by setting the offset amount of the wide portion 1b relative to the body portion 1a to 15 mm or more and 25 mm or less.

Furthermore, the fittability of the bone plate 1 to the tibia X can be enhanced while preventing interference between the tips of the screws 3c inserted into the screw holes 4c in the connecting portion 1c and the tips of the screws 3b inserted into the screw holes 4b in the wide portion 1b.

Figure 5:
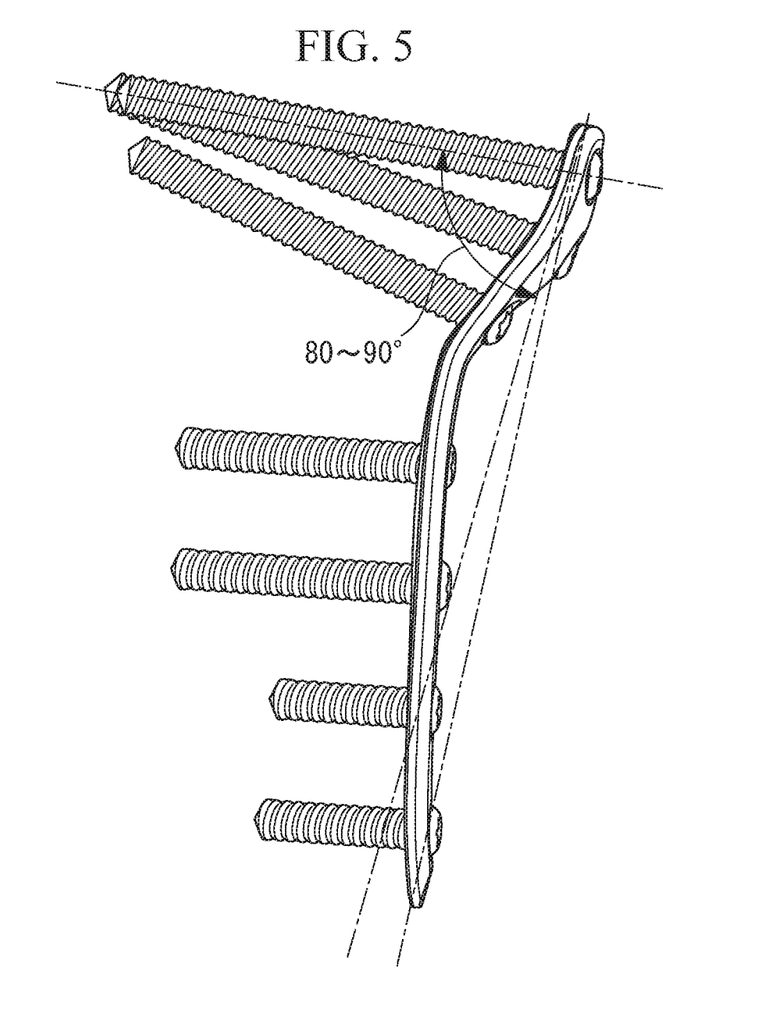
FIG. 5 is a side view illustrating an angle formed between an axis direction of a screw inserted into a wide portion and a straight line connecting an upper end portion and a lower end portion of the bone plate in the longitudinal direction.

In this embodiment, as illustrated in FIG. 5, the angle formed between a straight line connecting an upper end portion and a lower end portion of the bone plate 1 in the longitudinal direction and a plane that includes a straight line that defines the arraying direction of the screw holes 4b and the axis direction of the screw holes 4b is set to 80° or more and 90° or less so that the tips of the screws 3c inserted into the screw holes 4c in the connecting portion 1c can be positioned under the tips of the screws 3b inserted into the screw holes 4b in the wide portion 1b. Thus, the tips of the screws 3c inserted into the screw holes 4c in the connecting portion 1c are prevented from interfering with the tips of the screws 3b inserted into the screw holes 4b in the wide portion 1b. Moreover, since the screws 3c inserted into the screw holes 4c in the connecting portion 1c can be fastened so that tips thereof are delivered to a portion where the bone density is high, the fixability of the bone plate 1 can be enhanced.

The total length of the bone plate 1 in the longitudinal direction is set to 100 mm or more and 120 mm or less and preferably to 95 mm or more and 105 mm or less so that the bone plate 1 can closely follow the lateral surface of the tibia X despite the differences in the correction amount and the length of the tibia X attributable to differences in patient physical builds.

Stress shielding (the phenomenon in which the load is not smoothly exerted on the bone) of the tibia X under correction with the bone plate 1 attached thereto can be suppressed if a design is implemented such that the amount of deflection of the bone plate 1 when a vertical load W (the arrow direction indicated in FIG. 1) is applied in the longitudinal axis direction of the bone plate 1 (the bone axis direction of the tibia X) falls within the range of 0.5 mm±0.3 mm/kgf in a state in which the plate thickness of the bone plate 1 is set to about 3±1 mm and the bone plate 1 is fastened to the tibia X with the screws 3.

The bone plate 1 and the screws 3 are formed of a metal material having a high biocompatibility. Such a material has a relatively high safety to the human body even when it is installed in the human body.

The optimum biocompatible material used in the bone plate 1 and the screws 3 is a titanium alloy, which can maintain sufficient strength and elasticity over a long term. Naturally, the biocompatible material is not limited to titanium alloys, and other materials, such as cobalt chromium alloys, stainless steel, etc., can also be used.

Figure 6A:
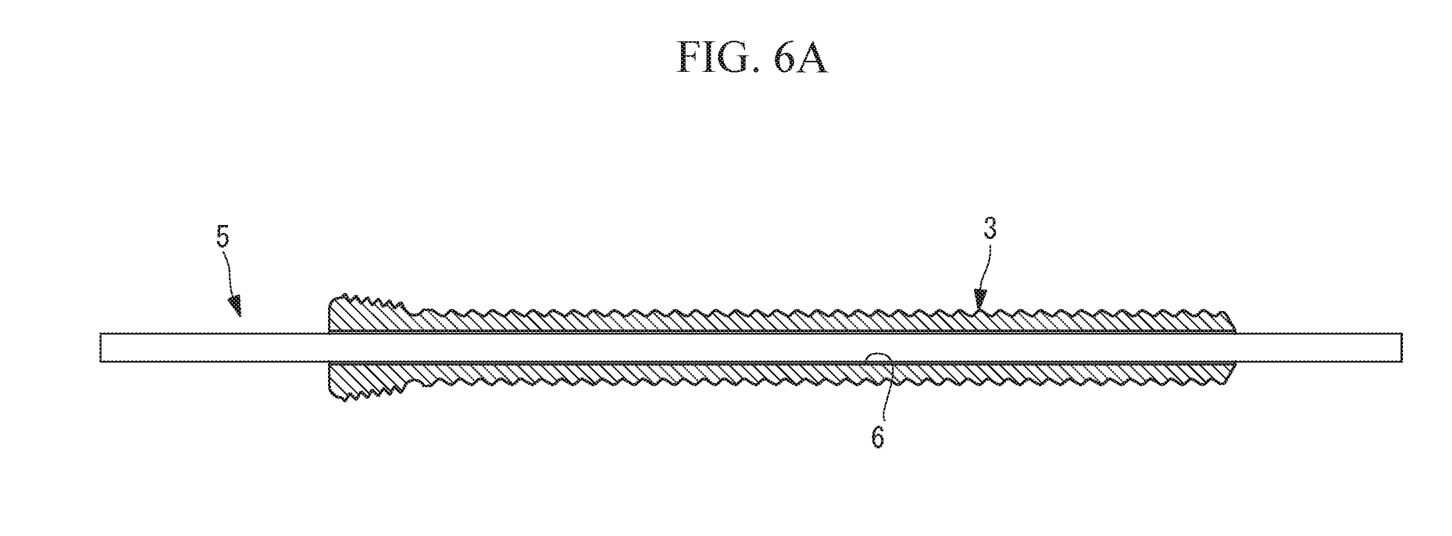
FIG. 6A is a diagram illustrating the case in which a guide pin is inserted into a screw used in the bone plate system illustrated in FIG. 1.
Figure 6B:
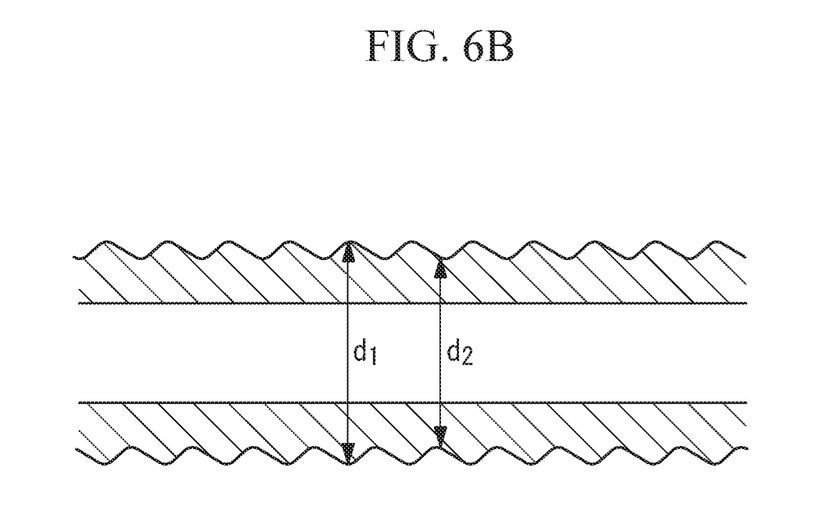
FIG. 6B is an enlarged view of a body portion of the screw illustrated in FIG. 6A.

As illustrated in FIGS. 6A and 6B, the screws 3 of this embodiment are hollow screws 3 each having a through hole 6 through which a guide pin 5 can pass. The thread diameter $d_1$ of the screws 3 may be set to φ5.0 mm or more and 5.8 mm or less, the root diameter $d_2$ may be set to φ4.5 mm or more and 5.3 mm or less, and the hollow shaft diameter $d_3$ of the screws 3 may be set to 01.8 mm or more and 2.8 mm or less.

The screws 3 of this embodiment are designed to have a diameter such that even when the screws 3 are fastened and fixed to the tibia X for a long time, the screws 3 sufficiently absorb the load in the vertical direction and remain unbroken. Moreover, by setting the diameters within these ranges, for example, in the epiphyseal region, the bone enters tip portions of the hollow holes, and thus the fixability can be improved.

Furthermore, since the diameters of the screws 3 are not excessively large, adverse effects caused by screw holes in the cancellous bone of the tibia X after removal of the bone plate 1 can be minimized.

Furthermore, since the screws 3 of this embodiment have through holes 6 through which the guide pins 5 can pass, the screws 3 can be fastened by using the through holes 6 in the screws 3 and the guide pins 5 as guides, and thus the operational ease of the fastening operation can be improved.

As a result, the following aspect is read from the above described embodiment of the present invention.

According to one aspect of the present invention, there is provided a bone plate comprising: a strip-shaped body portion to be fixed to a portion of the lateral surface of the tibia below an osteotomy surface formed in the lateral surface of the tibia, the body portion extending along a longitudinal direction of the tibia; a wide portion wider than the body portion and to be fixed along an outer peripheral surface of the head of the tibia at a higher position than the osteotomy surface; a connecting portion that connects the body portion and the wide portion; and a plurality of screw holes arrayed in the wide portion, the body portion, and the connecting portion with spaces between one another and penetrate therethrough in a plate thickness direction, wherein an inner surface that extends from the wide portion to the connecting portion and faces the tibia has a curved shape that substantially fits a three-dimensional contour of the tibia in a continuous manner while being twisted about an axis along the longitudinal direction of the tibia, the wide portion is offset in an outward plate thickness direction with respect to the body portion, and when the bone plate is attached to the tibia, a curvature of a side surface of the connecting portion that follows the posterior surface of the tibia is larger than a curvature of a side surface of the connecting portion that follows the anterior surface of the tibia.

According to the aspect described above, since the inner surface of the bone plate facing the tibia has a curved shape that substantially fits the three-dimensional contour of the tibia after hybrid HTO, the bone plate can be placed to follow the shape of the side surface of the tibia after the surgery.

Since the bone plate is designed for hybrid HTO, there is no need to preoperatively perform bending, sterilization treatment, etc., on the bone plate for fracture fixation, and preoperative preparation can be carried out easily.

Furthermore, since the curvature of the side surface of the connecting portion that follows the posterior surface of the tibia when the bone plate is attached to the tibia is larger than the curvature of the side surface of the connecting portion that follows the anterior surface of the tibia, the screws can be brought closer to one another in a direction orthogonal to the direction of the screws, and the number of engaging threads can be increased so as to enable more secure fixation. In addition, the tips of the screws inserted into the screw holes in the connecting portion can be assuredly delivered to the posterior portion of the tibia where the bone density of the tibia is large. As a result, even the portions that do not receive support from the osteotomy surface can be securely fixed.

In the aspect described above, the plurality of screw holes may include a plurality of first screw holes formed in the wide portion with spaces between one another, and a plurality of second screw holes formed in the connecting portion with spaces between one another, and a first axis, which is an axis of one of the plurality of the first screw holes that is located at a tibial posterior surface-side position when the bone plate is attached to the tibia, and a second axis, which is an axis of one of the plurality of the second screw holes that is located at a tibial anterior surface-side position when the bone plate is attached to the tibia, may lie along substantially the same plane.

In this manner, when the screws are inserted into the screw holes in the bone plate and fastened and fixed to the tibia, the tips of the screws can be accurately delivered to a posterior portion of the tibia where the bone density of the tibia is high. Thus, the fixability of the bone plate to the tibia can be enhanced. Moreover, even when a load is exerted in the vertical direction, the osteotomy surface of the tibia does not immediately receive the torque, and stable fixation can be achieved.

In the aspect described above, an angle formed between a straight line connecting an upper end portion and lower end portion of the bone plate in the longitudinal direction and a first plane that includes a straight line that defines an arraying direction of the plurality of first screw holes and an axis direction of the first screw holes may be 80° or more and 90° or less.

In this manner, the bone plate can closely follow the lateral surface of the tibia after correction despite the differences in the correction amount and the length of the tibia attributable to differences in patient physical builds.

Moreover, the screws can be inserted into the optimum range in which the articular surface remains unpierced and interference with artificial bones and defective parts of the bones is avoided.

In the aspect described above, an offset amount of the offset may be 15 mm or more and 25 mm or less.

In this manner, the bone plate can be placed to closely follow the lateral surface of the tibia after correction.

Moreover, the fittability of the bone plate to the tibia can be enhanced while preventing interreference between the tips of the screws inserted into the connecting portion and the tips of the screws inserted into the wide portion.

In the aspect described above, a total length in the longitudinal direction may be 100 mm or more and 120 mm or less and preferably 95 mm or more and 105 mm or less.

In this manner, the bone plate can be placed to appropriately fit the lateral surface of the tibia after the hybrid HTO is performed, despite the differences in the correction amount and the length of the tibia attributable to differences in the patient physical builds. In addition, since the bone plate is set within such dimensional ranges, the screws can be fastened in appropriate directions and at appropriate positions.

According to another aspect of the present invention, there is provided a bone plate system comprising: any of the bone plates described above and a plurality of screws to be respectively fastened to the plurality of screw holes in the bone plate so as to fix the bone plate to the tibia.

According to this aspect, since the inner surface of the bone plate facing the tibia has a curved shape that substantially fits the three-dimensional contour of the tibia after hybrid HTO, the bone plate can be placed to follow the shape of the side surface of the tibia after the surgery. Moreover, since the screws inserted into the screw holes in the bone plate are fastened so that the tips thereof are placed under the tibial articular surface, the screws can be fastened to a portion having a high bone density while avoiding piercing of the tibial articular surface.

Moreover, since the bone plate is designed not to project outward with respect to the head of the tibia, pain caused by a projecting bone plate stimulating the skin can be avoided.

In the aspect described above, the bone plate may have a plate thickness of 3±1 mm, and the bone plate system may be configured such that, in a state in which the bone plate is fastened with the plurality of screws, an amount of deflection of the bone plate when a vertical load is applied in a longitudinal axis direction of the bone plate is 0.5 mm±0.3 mm/kgf.

Since the amount of deflection of the bone plate is adjusted as such, stress shielding (the phenomenon in which the load is not smoothly exerted on the bone) of the tibia with the bone plate attached thereto can be suppressed.

In the aspect described above, the bone plate and the screws may contain a highly biocompatible material.

In this manner, an implant made of a highly biocompatible material having a sufficient strength and elasticity can be configured.

In the aspect described above, the screws may be hollow screws each having a through hole through which a guide pin can pass, a thread diameter of the screws may be φ5.0 mm or more and 5.8 mm or less, a root diameter may be φ4.5 mm or more and 5.3 mm or less, and a hollow shaft diameter of the hollow screws may be φ1.8 mm or more and 2.8 mm or less.

According to this aspect, the diameters are designed so that even when the bone plate is screwed to the tibia for a long time spanning years, the screws sufficiently absorb the load in the vertical direction and remain unbroken. By setting the diameters within these ranges, for example, in the epiphyseal region, the bone enters tip portions of the hollow holes, and thus the fixability can be improved.

Moreover, adverse effects caused by screw holes in the tibial cancellous bone after removal of the bone plate can be minimized.

Since the inner surface of the bone plate extending from the wide portion to the connecting portion has a twisted continuous curved shape, the screw fastening directions are not uniform, and errors are likely to occur regarding the screw fixing directions. However, according to the aspect described above, the screws have through holes through which guide pins can pass, and thus, the screws can be fastened by using the through holes in the screws and guide pins as the guides. Thus, the operational ease of the fastening operation can be improved.

REFERENCE SIGNS LIST 1 bone plate
1a body portion
1b wide portion
1c connecting portion
2 bone plate system
3, 3a, 3b, 3c screw
4, 4a, 4b, 4c screw hole
5 guide pin
6 through hole
X tibia
First axis A
Second axis B

The invention claimed is:

1. A bone plate comprising:
    a strip-shaped body portion extending along a longitudinal direction of a tibia, the strip-shaped portion being configured to fix to a portion of a lateral surface of the tibia on a first side of an incision formed in the lateral surface of the tibia;
    a wide portion having a width wider than a width of the body portion, the wide portion being configured to fix along an outer peripheral surface of a head of the tibia at a second side of the incision, the second side being closer to the head of the tibia than the first side;
    a connecting portion that connects the body portion and the wide portion; and
    a plurality of screw holes arrayed in the wide portion, the body portion, and the connecting portion with spaces between one another and penetrate therethrough in a plate thickness direction,
    wherein an inner surface that extends from the wide portion to the connecting portion and faces the tibia has a curved shape that substantially fits a three-dimensional contour of the tibia in a continuous manner while being twisted about an axis along the longitudinal direction of the tibia,
    the wide portion is offset in an outward plate thickness direction with respect to the body portion, and
    when the bone plate is attached to the tibia, a curvature of a side surface of the connecting portion that follows a posterior surface of the tibia is larger than a curvature of a side surface of the connecting portion that follows an anterior surface of the tibia.

2. The bone plate according to claim 1, wherein the plurality of screw holes comprise:
    a plurality of first screw holes formed in the wide portion with a first space between each of the plurality of first screw holes, and
    a plurality of second screw holes formed in the connecting portion with a second space between each of the plurality of second screw holes, and
    wherein a first axis, which is an axis of one of the plurality of the first screw holes that is located at a tibial posterior surface-side position when the bone plate is attached to the tibia, and a second axis, which is an axis of one of the plurality of the second screw holes that is located at a tibial anterior surface-side position when the bone plate is attached to the tibia, lie along substantially a same plane.

3. The bone plate according to claim 1, wherein an angle formed between a straight line connecting an upper end portion and lower end portion of the bone plate in the longitudinal direction and a first plane that includes a straight line that defines an arraying direction of the plurality of first screw holes and an axis direction of the first screw holes is between 80° and 90°.

4. The bone plate according to claim 1, wherein an offset amount of the offset is between 15 mm and 25 mm.

5. The bone plate according to claim 1, wherein a total length in the longitudinal direction is between 95 mm and 120 mm.

6. A bone plate system comprising:
    the plate according to claim 1; and
    a plurality of screws respectively fastened to the plurality of screw holes in the bone plate, the plurality of screws being configured to fix the bone plate to the tibia.

7. The bone plate system according to claim 6, wherein the bone plate has a plate thickness between 2 mm and 4 mm, and
    the bone plate system is configured such that, in a state in which the bone plate is fastened with the plurality of screws, an amount of deflection of the bone plate when a vertical load is applied in a longitudinal axis direction of the bone plate is between 0.2 mm and 0.8 mm when the vertical load is 1 kilogram.

8. The bone plate system according to claim 7, wherein the bone plate and the plurality of screws comprise a highly biocompatible material.

9. The bone plate system according to claim 7, wherein the plurality of screws are hollow, each having a through hole through which a guide pin can pass,
    a thread diameter of the plurality of screws is between 5.0 mm and 5.8 mm, and a root diameter of the plurality of screws is between 4.5 mm and 5.3 mm, and
    a hollow shaft diameter of the screws is between 1.8 mm and 2.8 mm.

* * * * *

UNITED STATES PATENT AND TRADEMARK OFFICE
CERTIFICATE OF CORRECTION

PATENT NO. : 10,905,480 B2  
APPLICATION NO. : 16/200760  
DATED : February 2, 2021  
INVENTOR(S) : Kuroda et al.

Page 1 of 1

It is certified that error appears in the above-identified patent and that said Letters Patent is hereby corrected as shown below:

On the Title Page

Item (73) Assignee should be corrected to read: OLYMPUS TERUMO BIOMATERIALS CORP., TOKYO (JP)

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*